(12) United States Patent
Fan

(10) Patent No.: US 10,848,648 B2
(45) Date of Patent: Nov. 24, 2020

(54) IMAGE SENSOR

(71) Applicant: OMNIVISION SEMICONDUCTOR (SHANGHAI) CO., LTD., Shanghai (CN)

(72) Inventor: Chun-Sheng Fan, Hsinchu (TW)

(73) Assignee: OMNIVISION SEMICONDUCTOR (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/560,239

(22) Filed: Sep. 4, 2019

(65) Prior Publication Data
US 2020/0266316 A1 Aug. 20, 2020

(30) Foreign Application Priority Data
Feb. 14, 2019 (CN) .......................... 2019 1 0113625

(51) Int. Cl.
| | |
|---|---|
| *H04N 5/225* | (2006.01) |
| *H01L 31/12* | (2006.01) |
| *H04N 5/378* | (2011.01) |
| *H04N 5/335* | (2011.01) |
| *H01L 31/107* | (2006.01) |
| *H01L 27/146* | (2006.01) |
| *H01L 31/0216* | (2014.01) |
| *H01S 5/026* | (2006.01) |
| *H01S 5/022* | (2006.01) |

(Continued)

(52) U.S. Cl.
CPC ....... *H04N 5/225* (2013.01); *H01L 27/14636* (2013.01); *H01L 27/14643* (2013.01); *H01L 31/02005* (2013.01); *H01L 31/02162* (2013.01); *H01L 31/107* (2013.01); *H01L 31/12* (2013.01); *H01S 5/0262* (2013.01); *H01S 5/02284* (2013.01); *H04N 5/2257* (2013.01); *H04N 5/3355* (2013.01); *H04N 5/378* (2013.01); *H01S 5/18369* (2013.01); *H04N 2005/2255* (2013.01)

(58) Field of Classification Search
CPC ......... H04N 2005/2255; H04N 5/2257; H04N 5/335–379; H04N 27/146
See application file for complete search history.

(56) References Cited

U.S. PATENT DOCUMENTS

| | | | |
|---|---|---|---|
| 10,313,356 B2 * | 6/2019 | Raynor | ................... G01S 17/10 |
| 2018/0048790 A1 * | 2/2018 | Adachi | ................ H04N 5/2353 |
| 2018/0136456 A1 * | 5/2018 | Watanabe | .......... G02B 23/2484 |

\* cited by examiner

*Primary Examiner* — Paul M Berardesca
(74) *Attorney, Agent, or Firm* — Womble Bond Dickinson (US) LLP

(57) ABSTRACT

An image sensor is disclosed which includes a substrate, a pixel array, a peripheral circuit, an SPAD detector and a VCSEL integrated in the substrate. The peripheral circuit is configured to process an electrical signal obtained from photoelectric conversion in the pixel array, the SPAD detector is configured to convert a first external optical pulse into an electrical pulse to provide a clock signal to the peripheral circuit. The VCSEL is driven by the peripheral circuit and configured to output a second optical pulse. The number of electrical connection terminals in the image sensor is reduced to only two, which is favorable to the miniaturization of the image sensor and simplifies the design of the mating device while allowing the inputting of a first optical pulse and outputting of a second optical pulse. By using these optical signals, extremely high speed and high bandwidth data transmission can be achieved.

14 Claims, 3 Drawing Sheets

(51) Int. Cl.
*H01L 31/02* (2006.01)
*H01S 5/183* (2006.01)

IMAGE SENSOR

CROSS-REFERENCE TO RELATED APPLICATION

This application claims the priority of Chinese patent application number 201910113625.1, filed on Feb. 14, 2019, the entire contents of which are incorporated herein by reference.

TECHNICAL FIELD

The present invention relates to the field of integrated circuits (ICs) and, in particular, an image sensor.

BACKGROUND

In the field of minimally invasive surgery, image sensors have been widely used, for example, in electro-endoscopes. Since an electro-endoscope is used to allow direct observation of an internal cavity or an organ's lumen in the body, in which it is inserted, it is required to have small dimensions. Accordingly, it is necessary for image sensors in such applications to be very small, for example, having a package size of 1.8 mm×1.8 mm, 1 mm×1 mm or even smaller. For image sensors imposed with such harsh requirements on compactness, the number and distribution of terminals on the image sensors for external electrical connection are critical. The electrical connection terminals generally include inputs and outputs for external electrical connection. For example, an existing image sensor includes four electrical connection terminals, which are used respectively as a power terminal, a ground terminal, a clock input and a signal output. The four electrical connection terminals are physically present on the image sensor in the form of solder balls typically having a diameter of 0.3 mm and residing on pads with a size of 1.2 mm and a pitch of 0.5 mm. Of course, these sizes may be properly adjusted to adapt to specific requirements, but all such adjustments must be made within the range of millimeters. Therefore, the electrical connection terminals are relatively bulky compared to the image sensor' package size, thus hindering the miniaturization of the image sensor. Additionally, the number of the electrical connection terminals on the image sensor is relative large, and as the mating device is required to have the same number of electrical connection terminals, it is possible to undesirably increase the structural complexity of the mating device. Further, this conventional image sensor usually communicates electrical signals, which tend to limit the transmission rate and experience attenuation and thus do not allow a large data transfer.

SUMMARY OF THE INVENTION

It is objective of the present invention to provide an image sensor having fewer terminals for external electrical connection while being able to transmit massive high-resolution image data at an increased transmission rate.

To this end, the provided image sensor includes a substrate, and a pixel array, a peripheral circuit, a single-photon avalanche diode detector and a vertical-cavity surface-emitting laser integrated in the substrate, the peripheral circuit configured to process an electrical signal obtained from photoelectric conversion in the pixel array, the single-photon avalanche diode detector configured to convert a first external optical pulse into an electrical pulse to provide a clock signal to the peripheral circuit, the vertical-cavity surface- emitting laser driven by the peripheral circuit and configured to output a second optical pulse, wherein the image sensor includes only two electrical connection terminals for external connection.

Optionally, the substrate may include a first surface and a second surface opposing the first surface, wherein the pixel array and solder pads surrounding the pixel array are provided on the first surface of the substrate, wherein the peripheral circuit is embedded in the substrate, wherein the solder pads include a power terminal for powering the image sensor and a ground terminal, and wherein the single-photon avalanche diode detector and the vertical-cavity surface-emitting laser are disposed on a side of the second surface of the substrate and are spaced apart from each other.

Optionally, the two electrical connection terminals may be provided on the side of the second surface of the substrate and respectively electrically connected to the power and ground terminals.

Optionally, the electrical connection terminals may be implemented as solder bumps.

Optionally, the second surface and a side surface of the substrate may be provided with an insulating layer, wherein openings spaced apart from each other are formed in a portion of the insulating layer over the second surface of the substrate, and wherein the single-photon avalanche diode detector and the vertical-cavity surface-emitting laser are disposed in different ones of the openings.

Optionally, the image sensor may further include a redistribution layer (RDL), wherein the electrical connection terminals are electrically connected to the solder pads through the redistribution layer.

Optionally, the redistribution layer may extend over the side surface of the substrate and terminates at the solder pads and the electrical connection terminals, and is electrically connected to the solder pads and the electrical connection terminals.

Optionally, the RDL may extend to, and thereby electrically connect, the solder pads and the electrical connection terminals by means of TSVs in the substrate.

Optionally, an optical band-pass filter coating may be provided on a surface of the SPAD detector.

Optionally, the SPAD detector and the VCSEL may operate in different frequency bands.

Optionally, the image sensor may further include an optical fiber configured to transfer the second optical pulse and an input power signal, the optical fiber coupled to the VCSEL.

Optionally, the image sensor may further include a supporting structure and a transparent baseplate, wherein the transparent baseplate covers the first surface of the substrate; the supporting structure is provided on the transparent baseplate so as to be sandwiched between the transparent baseplate and the substrate; and the substrate, the supporting structure and the transparent baseplate define a cavity in which the pixel array is received.

Optionally, a number of the vertical-cavity surface-emitting laser may be one.

Optionally, a plurality of VCSELs may be provided, each of VCSELs operating at a different frequency band.

Compared to the prior art, the image sensor provided in the present invention the substrate, pixel array, peripheral circuit, SPAD detector and VCSEL, as defined above. The SPAD detector is configured to convert a first external optical pulse into an electrical pulse which is then provided to the peripheral circuit as a clock signal. This dispense with the need to arrange a separate clock input as in the existing devices.

The VCSEL is driven by the peripheral circuit and configured to output a second optical pulse, thus further dispensing with the need to arrange a separate signal output as in the existing devices. As a result, the number of terminals for external electrical connection in the image sensor is reduced to only two, which is favorable to the miniaturization of the image sensor and simplifies the design of the mating device while allowing the inputting of a first optical pulse and outputting of a second optical pulse. By using these optical signals, the image sensor can transmit massive high-resolution image data at a high transmission rate, thus achieving extremely high speed, extremely high bandwidth data transmission.

In these figures: 11—substrate; 12—pixel array; 13—SPAD detector; 131—optical band-pass filter coating; 14—VCSEL; 15—solder pad; 16—electrical connection terminal; 16'—electrical connection terminal; 171—insulating layer; 172—insulating layer; 181—RDL; 182—RDL; 19—solder mask; 20—optical fiber; 21—support; 22—transparent baseplate; 23—cavity; 24—photoresist; 25—RDL; 26—carrier.

DETAILED DESCRIPTION OF THE INVENTION

A few specific embodiments of the invention will be described in greater detail with reference to the accompanying drawings. Features and advantages of the invention will become more apparent from the following description. Note that the drawings are provided in a very simplified form not necessarily drawn to scale, and their only intention is to facilitate convenience and clarity in explaining the embodiments.

Figure 1:
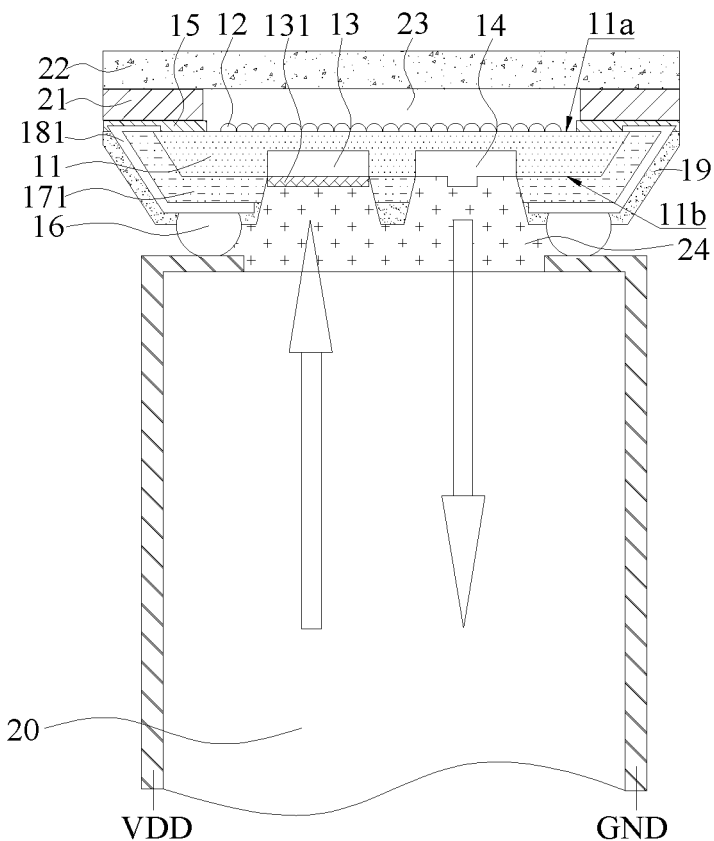
FIG. 1 is a schematic cross-sectional view of an image sensor according to an embodiment of the present invention.

The present invention provides an image sensor. Referring to FIG. 1, the image sensor according to an embodiment of the present invention includes:

a substrate 11, a pixel array 12 integrated to the substrate 11, a peripheral circuit (not shown), a single-photon avalanche diode (SPAD) detector 13 and a vertical-cavity surface-emitting laser (VCSEL) 14.

The peripheral circuit is configured to process an electrical signal resulting from photoelectric conversion in the pixel array 12.

The SPAD detector 13 is configured to convert a first external optical pulse into an electrical pulse which is then provided to the peripheral circuit as a clock signal.

The VCSEL 14 is driven by the peripheral circuit and is configured to output a second optical pulse.

The image sensor has only two external electrical connection terminals 16.

The external electrical connection terminals serve as interfaces of the image sensor for external electrical connection and interaction. The image sensor of the invention has only two electrical connection terminals 16. This means that the image sensor totally has only two electrical connection terminals which can meet its all needs for external input/output (I/O) activities during normal operation.

The substrate 11 on which the image sensor is formed may be, for example, a silicon or silicon-on-insulator (SOI) substrate. Material from which the substrate can be fabricated may further include germanium, silicon-germanium (SiGe), silicon carbide, gallium arsenide, indium gallium (InGa) or other III-V compounds.

The pixel array 12 may include millions of pixel cells each including, for example, a photodiode and a number of MOS transistors which constitute a driving circuit.

Figure 2:
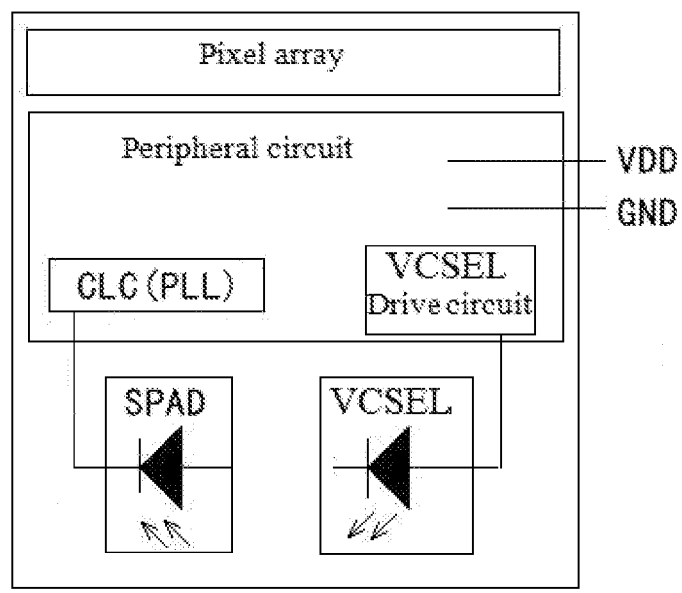
FIG. 2 schematically illustrates various modules in an image sensor according to an embodiment of the present invention.

With combined reference to FIGS. 1 and 2, the peripheral circuit (not shown) may be embedded in the substrate 11 and configured to process an electrical signal resulting from photoelectric conversion in the pixel array 12. The peripheral circuit may at least include a CLC (PLL) circuit and a VCSEL drive circuit. The CLC (PLL) circuit is the clock (phase-locked loop) circuit.

Figure 3:
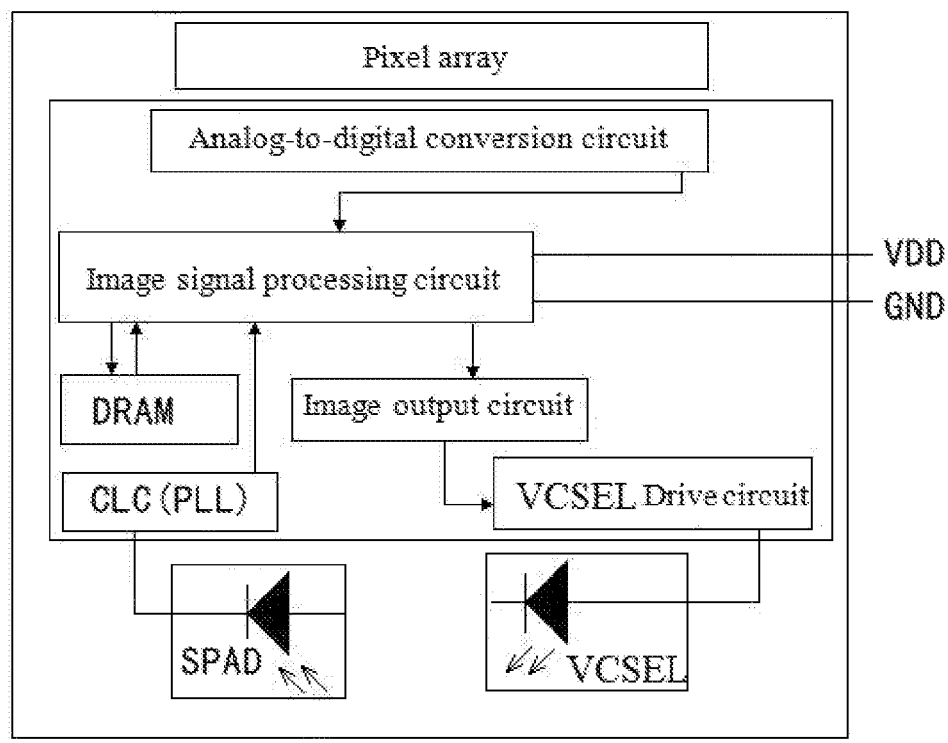
FIG. 3 schematically illustrates various modules in a particular example of a peripheral circuit in an image sensor according to an embodiment of the present invention.

Specifically, with combined reference to FIGS. 1 and 3, the peripheral circuit may specifically include an analog-to-digital (A/D) conversion circuit, an image signal processing circuit, a dynamic random-access memory (DRAM) circuit, the clock (phase-locked loop) circuit, an image output circuit, the VCSEL drive circuit and the like. The A/D convert circuit may be configured to produce a digital signal by carrying out A/D conversion on a signal output from the pixel array. The image signal processing circuit may be configured to process the digital signal and pass it on to the image output circuit. The DRAM circuit may interact with the image signal processing circuit and function as a buffer to store the image signal which may be then output in accordance with the processing speed of the image signal processing circuit in order to ensure image quality.

The SPAD detector may be configured to convert a first external optical pulse into an electrical pulse which is then fed to the peripheral circuit as a clock signal for the CLC PLL circuit therein. The VCSEL may be driven by the VCSEL drive circuit in the peripheral circuit and configured to output a second optical pulse.

The SPAD detector 13 may include an SPAD, a quenching circuit and a readout circuit. The SPAD is able to capture single photons with an extremely high arrival time resolution on the order of tens of picoseconds and produce electrical pulses from collision of the photons. In the SPAD, a p-n junction is reverse-biased at a level well above the breakdown voltage of the junction. At this bias, the electric field is so high that a single charge carrier injected into the depletion layer can trigger a self-sustaining avalanche. The leading edge of the avalanche current pulse marks the arrival time of the detected photon. The current continues until the avalanche is quenched by lowering the bias voltage down to or below the breakdown voltage. The quenching of the avalanche is performed by the quenching circuit, which may include a high-resistance ballast load in series with the SPAD, or may alternatively include active circuit elements. The intensity of the photon signal received by the SPAD may be detected by counting the number of output electrical pulses, so the readout circuit may include a number of counters.

The VCSEL may be a "sandwich" structure consisting of an upper distributed Bragg reflector (DBR), an active region and a lower DBR. The two DBRs form a resonant cavity together with the active region, from which a laser beam will be emitted perpendicular to the surface of the substrate. The active region contains a number of quantum wells and is a key component that determines some important parameters of the device, such as threshold gain and lasing wavelength. Each of the DBRs is made up of a high-reflectivity multilayer dielectric film and can thus reflect light. The formation of the laser beam involves energy excitation and resonant amplification. First of all, the VCSEL drive circuit applies external energy (electric) to excite electrons in the semiconductor active region, causing a transition of the electrons from the valence band to the conduction band. Upon the electrons falling back to the valence band from the conduction band, the energy is released in the form of a light beam, which is then reflected back and forth between the two DBRs and, in this course, continuously increases its energy until resonance occurs. As a result, the light beam is amplified in energy and forms the laser beam. The VCSEL is advantageous in a small divergence angle, low power consumption, high uniformity and a high coupling level with fiber optics.

The pixel array, the peripheral circuit, the SPAD detector and the VCSEL may be integrated to the substrate.

In an embodiment, the substrate, the pixel array, the peripheral circuit, the SPAD detector and the VCSEL may be integrally incorporated in a single die.

In another embodiment, the substrate, the pixel array and the peripheral circuit may be formed in a single die, while the SPAD detector and the VCSEL may be incorporated in respective separate dies. The SPAD detector and the VCSEL may be integrated to the substrate either by bonding or an adhesion. The bonding may be accomplished at the wafer-level and followed by dicing or at the die-level.

With continued reference to FIG. 1, the substrate 11 may have a first surface 11a and a second surface 11b opposite the first surface 11a. The pixel array 12 and the solder pads 15 surrounding the pixel array 12 are arranged on the first surface 11a of the substrate. The pixel array 12 may include the aforementioned photodiodes, as well as, a plurality of color filters, both for converting an incident light beam into an electrical signal. The solder pads 15 may provide a power terminal for powering the image sensor and a ground terminal. It will be appreciated that the relative positions of the pixel array 12 and the solder pads 15 of the substrate 11 may vary depending on different requirements. For example, the solder pads 15 may be on either or both sides of the pixel array 12. The peripheral circuit may be embedded in the substrate 11. The SPAD detector 13 and the VCSEL 14 may also be formed spaced apart on the side where the second surface 11b of the substrate 11 is located.

The electrical connection terminals 16 may be provided on the side of the second surface 11b of the substrate 11. The number of the electrical connection terminals 16 may be two and the two electrical connection terminals are respectively electrically connected to the power and ground terminals.

An insulating layer 171 may be provided, which covers the second surface 11b and a side surface of the substrate 11. Openings spaced apart from each other may be formed in the portion of the insulating layer 17 on the second surface of the substrate, in which the SPAD detector 13 and the VCSEL 14 are respectively received.

The image sensor may further include a redistribution layer (RDL) 181, the electrical connection terminals 16 are electrically connected to the solder pads 15 through the RDL 181.

In one embodiment, the RDL 181 may partially cover the surface of the insulating layer 171. The redistribution layer (RDL) 181 is distributed along the side of the substrate 11 and extends to the solder pads 15 and the electrical connection terminals 16, respectively, and thereby electrically connects the solder pads 15 and the electrical connection terminals 16.

A solder mask 19 may be formed over the insulating layer 171 and the RDL 181. It may define openings in which the surface of the RDL 181 is exposed. The solder mask 19 may be formed of, for example, lacquer for effective protecting the RDL 181 from oxidation, short circuit and the like. The electrical connection terminals 16 are received in the openings. The electrical connection terminals 16 and are electrically connected to the RDL 181. Specifically, the electrical connection terminals 16 may be provided in the form of solder bumps, such as solder balls, metal posts or the like and made of tin, aluminum (Al), gold (Au), copper (Cu), lead or any other suitable metallic material. The RDL may be a thin film made of a metallic material such as Al, Au or Cu. The RDL allows rewiring of metal buses so that the positioning of the terminals 16 for electrical connection of the image sensor is optimized to meet the minimum spacing requirement between the electrical connection terminals.

Figure 4:
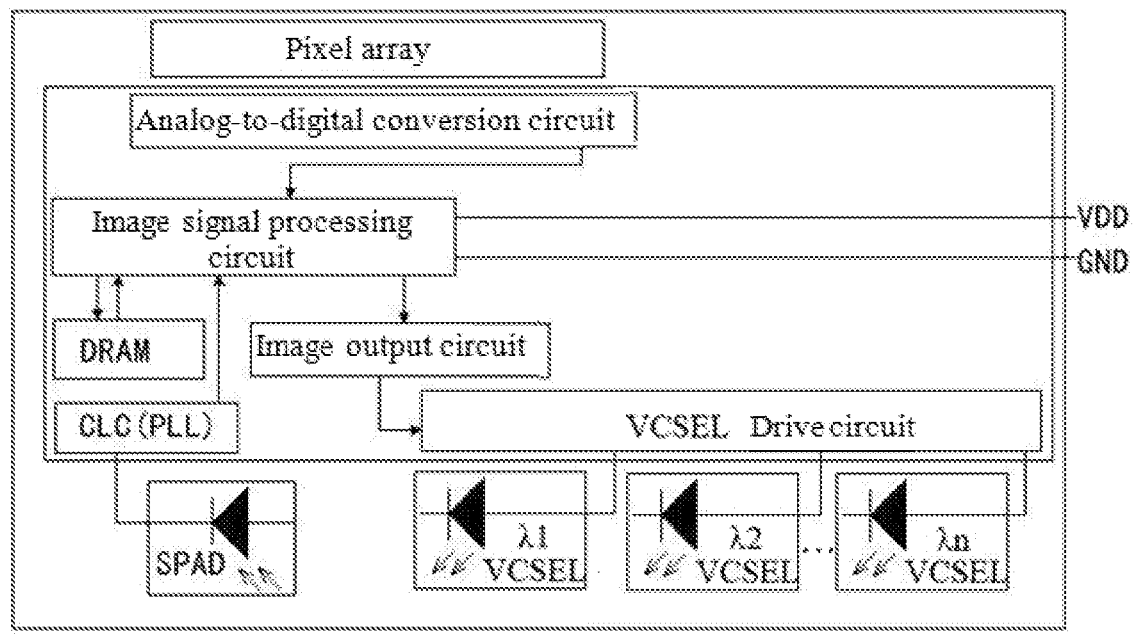
FIG. 4 schematically illustrates an image sensor including a plurality of VCSEL modules according to an embodiment of the present invention.

As shown in FIG. 4, in one embodiment, the image sensor may include a plurality of VCSELs each operating at a different frequency band so that the image sensor can have an expanded output bandwidth. The image sensor may encode an image into multimode signals which may then be transmitted at various wavelengths ($\lambda 1$-$\lambda n$) from the VCSELs via fiber optics to a decoder for decoding the multimode signals into signals at the various wavelengths.

Figure 5:
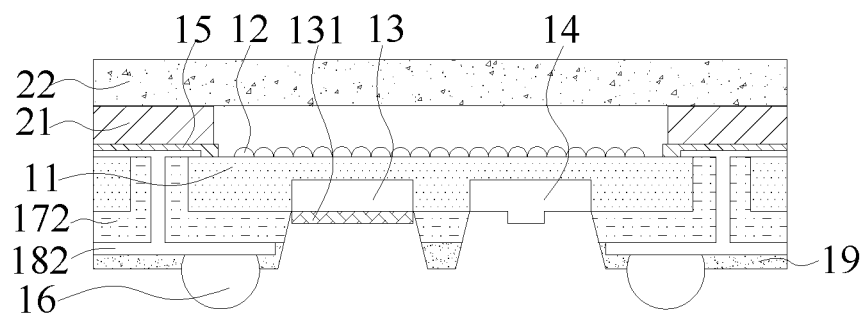
FIG. 5 is a schematic cross-sectional view of an image sensor according to another embodiment of the present invention.

As shown in FIG. 5, according to another embodiment, the RDL 182 may be electrically connected to the solder pads 15 and the electrical connection terminals 16 by means of through silicon vias (TSVs) in the substrate 11. In this case, the insulating layer 172 may cover the second surface of the substrate 11 and the side surfaces of the TSVs.

Figure 6:
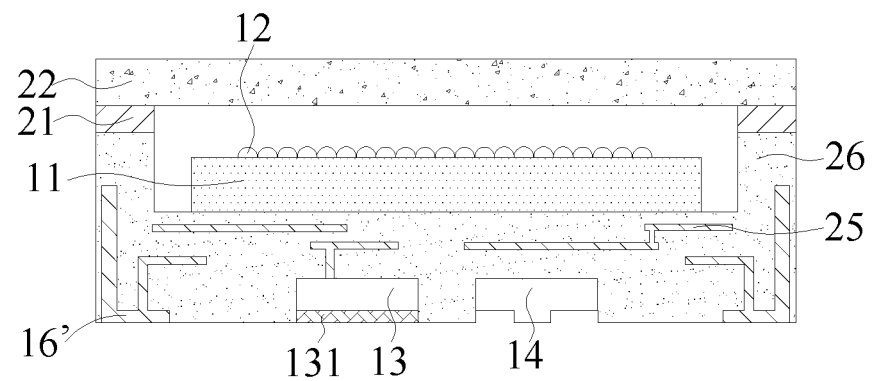
FIG. 6 is a schematic cross-sectional view of an image sensor according to still another embodiment of the present invention.

As shown in FIG. 6, according to still another embodiment, the substrate 11, the pixel array 12 and the peripheral circuit may be all formed in a single die, wherein the substrate 11 is supported on a carrier 26, the RDL 25 is embedded in the carrier 26. Two electrical connection terminals 16' lead from the RDL 25 to the surface of the carrier 26. The two electrical connection terminals 16' may be respectively electrically connected to the power terminal for powering the image sensor and the ground terminal. The SPAD detector 13 and the VCSEL 14 may be both buried in the carrier 26 and spaced apart from each other. The SPAD detector 13 may be electrically connected to the CLC PLL circuit in the peripheral circuit via the RDL 25. The VCSEL 14 may be electrically connected to the VCSEL drive circuit in the peripheral circuit via the RDL 25. The carrier 26 may be, for example, a CLCC, PLCC, QFN or any other suitable carrier.

As shown in FIGS. 1, 5 and 6, an optical band-pass filter coating 131 may be provided on the surface of the SPAD detector 13. The optical band-pass filter coating 131 may allow the passage of a narrow infrared wavelength band of, for example, any one of 850 nm, 940 nm, 1260 nm and 1550 nm.

The SPAD detector 13 and the VCSEL 14 may operate at different frequency bands in order to avoid crosstalk. For example, the SPAD 13 may operate at an infrared wavelength of 850 nm, while the VCSEL 14 may emit signals at 1550 nm. Such a large gap between the operating frequencies is desirable for reducing noise and preventing crosstalk.

With continued reference to FIG. 1, the image sensor may further include an optical fiber 20. The optical fiber 20 is configured to transfer the second optical pulse and an input power signal and the optical fiber 20 is coupled to the VCSEL 14. In one embodiment, the optical fiber 20 may include an optical fiber for transmitting the second optical pulse and two optical fibers, which are electrically coupled to the respective electrical connection terminals 16 in order to transmit the input power signal. According to another embodiment, the optical fiber 20 may include an optical fiber for transferring the second optical pulse and two metal-plated electrodes running in parallel to the optical fiber for transferring the second optical pulse. These two metal-plated electrodes may be configured to transmit the input power signal and electrically connected to the respective electrical connection terminals 16. In order to facilitate the coupling of the second optical pulse from the VCSEL 14 into the optical fiber, transparent photoresist 24 may be filled in a gap between the image sensor and the optical fiber 20.

The image sensor may further include a supporting structure 21 and a transparent baseplate 22. The transparent baseplate 22 may cover the first surface 11a of the substrate 11, and the supporting structure 21 may be provided on the transparent baseplate 22, the supporting structure 21 is sandwiched between the transparent baseplate 22 and the substrate 11. The substrate 11, the supporting structure 21 and the transparent baseplate 22 may define a cavity 23, the pixel array 12 is received in the cavity 23.

The transparent baseplate 22 may be configured to protect the pixel array 12 from damage or contamination. Since the transparent baseplate 22 is required to allow light to pass therethrough to reach the pixel array 12, it may be made of a high light-transmittance material. Specifically, materials from which the transparent baseplate can be fabricated may include inorganic glass, organic glass and any other suitable light-transmissive material with proper strength. The transparent baseplate may have a uniform, smooth surface that will not cause scattering or diffuse reflection of the incident light. The supporting structure 21 may be attached to the surface of the transparent baseplate closer to the substrate 11. The supporting structure 21 may be made of a photo-sensitive material such as black photoresist. The material may be applied, by spraying or spinning, to the surface of the transparent baseplate closer to the substrate 11 and then patterned, by exposure and development, to form the supporting structure 21. In alternative embodiments, the supporting structure may also be formed by depositing silicon oxide, silicon nitride, silicon oxynitride or any other suitable insulating dielectric material and then patterning the deposited material by photolithography and etching techniques. Further, an adhesive layer (not shown) for adhesion, insulation and sealing may be disposed between the supporting structure 21 and the first surface 11a of the substrate 11.

In summary, the present invention relates to an image sensor including a substrate, a pixel array integrated to the substrate, a peripheral circuit, an SPAD detector and a VCSEL. The SPAD detector is configured to convert a first external optical pulse into an electrical pulse which is then provided to the peripheral circuit as a clock signal. This dispenses with the need to arrange a separate clock input as in the existing devices. The VCSEL is driven by the peripheral circuit and configured to output a second optical pulse, thus further dispensing with the need to arrange a separate signal output as in the existing devices. As a result, the number of terminals for external electrical connection in the image sensor is reduced to only two, which is favorable to the miniaturization of the image sensor and simplifies the design of the mating device while allowing the inputting of a first optical pulse and outputting of a second optical pulse. By using these optical signals, the image sensor can transmit massive high-resolution image data at a high transmission rate, thus achieving extremely high speed, extremely high bandwidth data transmission.

It is noted that the embodiments disclosed herein are described in a progressive manner, with the description of each embodiment focusing on its differences from others. Reference can be made between the embodiments for their identical or similar parts. Since the method embodiments correspond to the apparatus embodiments, they are described relatively briefly, and reference can be made to the apparatus embodiments for details in the method embodiments.

The description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. An image sensor, comprising
    a substrate, and
    a pixel array, a peripheral circuit, a single-photon avalanche diode detector and a vertical-cavity surface-emitting laser integrated in the substrate,
    the peripheral circuit configured to process an electrical signal obtained from photoelectric conversion in the pixel array,
    the single-photon avalanche diode detector configured to convert a first external optical pulse into an electrical pulse to provide a clock signal to the peripheral circuit,
    the vertical-cavity surface-emitting laser driven by the peripheral circuit and configured to output a second optical pulse,
    wherein the image sensor comprises only two electrical connection terminals for external connection.

2. The image sensor of claim 1, wherein the substrate comprises a first surface and a second surface opposing the first surface, wherein the pixel array and solder pads surrounding the pixel array are provided on the first surface of the substrate, wherein the peripheral circuit is embedded in the substrate, wherein the solder pads comprise a power terminal for powering the image sensor and a ground terminal, and wherein the single-photon avalanche diode detector and the vertical-cavity surface-emitting laser are disposed on a side of the second surface of the substrate and are spaced apart from each other.

3. The image sensor of claim 2, wherein the two electrical connection terminals are provided on the side of the second surface of the substrate and are respectively electrically connected to the power terminal and the ground terminal.

4. The image sensor of claim 3, wherein the electrical connection terminals are implemented as solder bumps.

5. The image sensor of claim 4, wherein the second surface and a side surface of the substrate are provided with an insulating layer, wherein openings spaced apart from each other are formed in a portion of the insulating layer over the second surface of the substrate, and wherein the single-photon avalanche diode detector and the vertical-cavity surface-emitting laser are disposed in different ones of the openings.

6. The image sensor of claim 5, further comprising a redistribution layer, wherein the electrical connection terminals are electrically connected to the solder pads through the redistribution layer.

7. The image sensor of claim 6, wherein the redistribution layer extends over the side surface of the substrate and terminates at the solder pads and the electrical connection terminals, and is electrically connected to the solder pads and the electrical connection terminals.

8. The image sensor of claim 6, wherein the redistribution layer extends to, and thereby electrically connects, the solder pads and the electrical connection terminals by means of TSVs in the substrate.

9. The image sensor of claim 1, wherein an optical band-pass filter coating is provided on a surface of the single-photon avalanche diode detector.

10. The image sensor of claim 1, wherein the single-photon avalanche diode detector and the vertical-cavity surface-emitting laser operate in different frequency bands.

11. The image sensor of claim 1, further comprising an optical fiber configured to transfer the second optical pulse and an input power signal, the optical fiber coupled to the vertical-cavity surface-emitting laser.

12. The image sensor of claim 1, further comprising a supporting structure and a transparent baseplate, the transparent baseplate covering the first surface of the substrate, the supporting structure provided on the transparent baseplate so as to be sandwiched between the transparent baseplate and the substrate, the substrate, the supporting structure and the transparent baseplate defining a cavity in which the pixel array is received.

13. The image sensor of claim 1, wherein a number of the vertical-cavity surface-emitting laser is one.

14. The image sensor of claim 1, wherein a plurality of vertical-cavity surface-emitting lasers are provided, each of the plurality of vertical-cavity surface-emitting lasers operating at a different frequency band.

* * * * *